US006962963B2

(12) United States Patent
Kumar et al.

(10) Patent No.: US 6,962,963 B2
(45) Date of Patent: Nov. 8, 2005

(54) ENZYMATIC SYNTHESIS OF POLYMERS

(75) Inventors: Rajesh Kumar, Lowell, MA (US);
Arthur C. Watterson, Nashua, NH (US); Virinder Singh Parmar, Lowell, MA (US); Jayant Kumar, Westford, MA (US); Lynne Ann Samuelson, Marlboro, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/688,582

(22) Filed: Oct. 17, 2003

(65) Prior Publication Data

US 2004/0152176 A1 Aug. 5, 2004

Related U.S. Application Data

(60) Provisional application No. 60/419,478, filed on Oct. 18, 2002.

(51) Int. Cl.[7] ................. C08G 77/08; C08G 77/26; C08G 77/445
(52) U.S. Cl. .................. 528/26; 528/28; 528/21
(58) Field of Search .................. 528/26, 28, 21

(56) References Cited

U.S. PATENT DOCUMENTS

| | | | | |
|---|---|---|---|---|
| 5,070,069 | A | * 12/1991 | Bradbury et al. | 503/227 |
| 5,631,343 | A | * 5/1997 | Binns et al. | 528/274 |
| 6,288,129 | B1 | * 9/2001 | Gruning et al. | 516/23 |
| 6,486,295 | B1 | * 11/2002 | Gross et al. | 528/354 |
| 6,617,411 | B1 | * 9/2003 | Friedrich | 528/21 |
| 6,670,438 | B1 | * 12/2003 | Morse et al. | 528/21 |
| 6,677,427 | B1 | * 1/2004 | Cheng et al. | 528/310 |

OTHER PUBLICATIONS

Bisht et al., *Am. Chem. Soc.*, vol. 120, p. 1363, 1998.
Bruma et al., *J. Macromol. Sci. Polymer Reviews*, vol. C41 (1 & 2), p. 1, 2001.
Chaudhary et al., Biocatalytic Solvent–free Polymerization to Produce High Molecular Weight Polyesters, *Biotechnol. Prog.*, vol. 13, pp. 318–325, 1997.
Chojnowski et al, *Polymer Preprints*, vol. 42(1), p. 227, 2001.
Cordova et al., *Micromolecules*, vol. 31, p. 1040, 1998.
Gross et al., Enzymes in Polymers Synthesis Ed., *ACS Symp. Ser.* 1998.
Gross et al., A. Polyesters and Polycarbonate Synthesis by InVitro Enzyme Catalysis, *Appl. Microbial. Biotechnol.*, vol. 55, pp. 655–660, 2001.
Gross et al., Polymer Synthesis by in vitro Enzyme Catalysis, *Chem. Rev.*, vol. 101, pp. 2097–2124, 2001.
Interrante et al., *Polymer Preprints*, vol. 42(1), p. 225, 2001.
Jones, Enzymes in Organic Synthesis, *Tetrahedron.*, vol. 42, pp. 3351–3403, 1986.

Klibanov, Asymmetric transformation catalyzed by enzymes in organic solvents, *Acc Chem. Res.*, vol. 23, pp. 114–120, 1990.
Kline, et al. One–step Biocatalytic Synthesis of Linear Polyesters with Pendant Hydroxyl Groups, *J. Am Chem. Soc.*, vol. 120, pp. 9475–9480, 1998.
Kobayashi et al., The Polymeric Materials Encyclopedia, *JC Salamone, Ed.*, CRC Press, BocaRaton, FL, pp. 2102–2107, 1996.
Kobayashi et al., Catalysis in Precision Polymerization, Kobayashi, S. Ed., John Wiley & Sons, *Chichester* Chapter 8, 1997.
Kobayashi et al., *Macromolecules*, vol. 31, p. 5655, 1998.
Kobayashi et al., *Polym. Degrad.Stab.*, vol. 59, p. 195, 1998.
Kobayashi et al., *Adv. Polym. Sci.*, vol. 121, p. 1, 1991.
Kobayashi et al., Enzymatic Polymerization, *Chem. Rev.*, vol. 101, pp. 3793–3818, 2001.
Kumar et al., Chemo Enzymatic Synthesis of Novel Functionalized Amphiphilic Polymers, *Polymer Preprints*, vol. 43(1), p. 578, 2002.
Santaniello et al., The biocatalytic approach to the preparation of enantiomerically pure chiral building blocks, *Chem. Rev.*, vol. 92, pp. 1071–1140, 1992.
Suda, et al., Dehydration Polycondensation in Water for Synthesis of Polyesters by Lipase Catalysis, *Proc. Acad. Jp.*, vol. 75B, pp. 201–206, 1999.
Torchilin, Structure and design of polymeric surfactant–based drug delivery systems, J. Contr. Rel., vol. 73, pp. 137–172, 2001.
Uyama et al., *Chem. Lett.*, pp. 1149, 1993.
Uyama et al., Enzymatic Polymerization of Dicarboxylic Acid and Glycol to Polyester in Solvent–Free System, *Chemistry Letters.*, pp. 1285–1286, 1998.
Uyama et al., Enzymatic Synthesis of Aromatic Polyesters by Lipase–Catalyzed Polymerization of Discarboxylic Acid Divinyl Esters and Glycols, *Polymer Journal.*, vol. 31, pp. 383–386. 1999.
Uyama, et al. Lipase–Catalyzed Polycondensation of Dicarboxylic acid Divinyl esters and Glycols to Aliphatic Polyesters, *J. Polym. Sci., Polym. Chem. Ed.*, vol. 37, pp. 2737–2745, 1999.
Uyama et al., Lipase–Catalyzed Polycondensation of Discarboxylic acid Divinyl esters and glycols to aliphatic polyesters, *J. Polym. Sci., Polym.Chem.Ed.*, vol. 37, pp. 2737–2745, 1999.
Watterson et al., Observing the Aggregation of a Novel Amphiphilic Polymer in Solution using $^1$H–NMR Relaxation Times (TI), *Polymer Preprints.*, vol. 42, pp. 189–190, 2001.
Zhong et al, *Langmuir*, vol. 16, p. 10369, 2000.

* cited by examiner

*Primary Examiner*—Margaret G. Moore
(74) *Attorney, Agent, or Firm*—Fish & Richardson P.C.

(57) ABSTRACT

The invention relates to new methods of enzymatic synthesis of polymers such as polyorganosilicones and polyesters, and new polymers made by these methods.

16 Claims, 2 Drawing Sheets

ENZYMATIC SYNTHESIS OF POLYMERS

CROSS-REFERENCE TO RELATED APPLICATION

This application claims priority from U.S. Provisional Patent Application No. 60/419,478, filed on Oct. 18, 2002, the contents of which are incorporated herein by reference in their entirety.

TECHNICAL FIELD

This invention relates to polymers and their synthesis, and more particularly to silicon-based polymers and polyesters, as well as enzymatic synthesis of these polymers.

BACKGROUND

Polymers, such as polyorganosilicones and polyesters, can be found in every corner of today's society due to their excellent mechanical and chemical properties. Polyorganosilicones, including polysilanes and polycarbosiloxanes, have interesting properties such as photo-conductivity and luminescence, and possess high thermal stability at the same time. See, e.g., Chojnowski et al., Polymer Preprints, 42, 227 (2001); Interrante et al., Polymer Preprints, 42, 225 (2001); Zhong et al., Langmuir, 16, 10369 (2000); and Bruma et al., J. Macromol. Sci. Polymer Reviews, C41, 1 (2001). Polyesters, on the other hand, because of their degradability, can be used in biomedical applications such as sustained-release drug delivery. See, e.g., Kopecek et al., J. Biomed. Mater. Res. Symp., 1, 43 (1971).

These polymers have been traditionally prepared by chemical synthesis, which normally consumes large quantities of solvents and starting materials, which, in turn, can damage the environment. Environment-friendly synthetic methods for making such polymers are therefore highly desirable.

SUMMARY

The invention is based, in part, on the discovery that certain enzymes can be used to catalyze the polymerization of polyorganosilicone or alkylene glycol-based polyester under mild and environmentally friendly reaction conditions.

In one aspect, this invention relates to new enzymatic methods of synthesizing a polymer. Each of the methods includes the steps of mixing monomers, adding an enzyme, e.g., a lipase, esterase, or protease, to the monomer mixture to form a reaction mixture, and reacting the reaction mixture for a time and under polymerizing conditions suitable to obtain a polyorganosilicone polymer or an alkylene glycol-based polyester polymer.

The term "monomer" refers to a molecule that can undergo a polymerization process, e.g., through condensation polymerization or addition polymerization. Specifically, the monomers that can be used to practice the methods of this invention include linear monomers (i.e., non-cyclic, including graft monomers) or cyclic monomers, oligomers, macromers, and mixtures thereof. Each of the monomers, oligomers, and macromers can be monofunctional, bifunctional, trifunctional, or multifunctional. Examples of suitable monomers include, but are not limited to, diacids and diols, diacids and diamines, anhydrides and diols, and anhydrides and diamines.

The term "alkylene glycol" refers to a moiety consisting of an alkylene sub-moiety (e.g., ethylene, butylene, and hexylene) and a second sub-moiety that is either oxygen, sulfur, or amino.

Embodiments of the methods include those in which the polymer is a multi-component polyester (e.g., terpolymer or tetrapolymer) wherein at least three components are aliphatic, aromatic, or cyclic monomers, or combinations thereof; those in which the monomers are diacids and diols; those in which the polymers are polyorganosilicones; and those in which the polymers are polyesters. The term "polyorganosilicones" refers to those polymers containing at least one silicone (i.e., siloxane) moiety (e.g., dimethylsiloxane). The term "polyesters" refers to those polymers containing at least one ester linkage.

Examples of polyorganosilicones that can be made by the new methods include those of formula (I):

In this formula, each of R, independently, is a hydroxy, or amino; each R', independently is a hydroxy or alkoxy; each R", independently is a hydrogen, alkyl, alkoxy, aryl, or aryloxy; each x, independently, is an integral of 1 to 10; y is an integral of 1 to 1,000; n is an integral of 1 to 10,000; and each of A, independently, is O or NH; and B, independently, is a linear or cyclic alkylene, arylene, or oxaalkylene.

As used herein, the term "alkyl" refers to $C_{1-12}$ straight-chain or $C_{3-12}$ branched hydrocarbons, e.g., methyl, isobutyl, and hexyl; the term "alkoxy" refers to alkyl connected to a main chain or backbone through an oxygen atom (i.e., —O-alkyl); the term "aryl" refers to aromatic rings such as phenyl, pyridinyl, thienyl, thiazolyl, and furyl, optionally substituted with one or more groups such as halo (e.g., fluro), haloalkyl (e.g., trichloromethyl), amino, or alkyl (e.g., t-butyl); and, like "alkoxy," the term "aryloxy" refers to aryl groups that are attached to a main chain or backbone through an oxygen atom (i.e., —O-aryl).

The new polyorganosilicones described herein can be prepared, e.g., by an enzymatic polymerization reaction, e.g., between a silicone monomer containing end hydroxy or amino groups, and another monomer such as a diacid or diester; or between a silicone monomer containing end carboxy or ester groups, and another monomer such as a diamines.

Examples of polyesters that can be made by the new methods also include those of formula (II):

In this formula, each of R and R', independently, is a hydrogen, hydroxy, amino, alkoxy, aryl, or aryloxy; each x, independently, is an integral of 1 to 10; n is an integral of 1 to 10,000; each T, independently, is alkyl or aryl; and each of A and B, independently, is a linear or cyclic alkyl, aryl, or alkoxy.

Additional examples of polyesters that can be made by the new methods include those of formula (III):

(III)

In this formula, each of R and R', independently, is a hydrogen, hydroxy, amino, alkoxy, aryl, or aryloxy; each x, independently, is an integral of 1 to 10; n is an integral of 1 to 10,000; each T, independently, is alkyl or aryl; and each of A and B, independently, is oxygen, sulfur, amino, or a linear or cyclic alkyl.

Further examples of polyesters that can be made by the new methods include those of formula (IV):

(IV)

In this formula, each of R and R', independently, is a hydrogen, hydroxy, amino, alkoxy, aryl, or aryloxy; each of x and y, independently, is an integral of 1 to 10; n is an integral of 1 to 10,000; each T, independently, is alkyl or aryl; and each of A and B, independently, is oxygen, sulfur, amino, alkyl, or aryl.

Another aspect of this invention relates to the polyorganosilicones described herein. Specific examples of these polyorganosilicones include those in which T is alkylene (e.g., ethylene); those in which A is oxygen or amino; those in which x is 2–6; those in which B is oxygen or amino; and those in which each of R and R', independently, is hydroxy or amino.

Other aspects of the invention include compositions, structures, or devices containing one or more of the new polyorganosilicones, and methods of preventing fire by using as a fire-retardant one or more of the new polyorganosilicones.

The invention also relates to methods of incorporating a third monomer into a preformed polymer by using one of the enzymes described herein (e.g., lipase), wherein the monomer can be a linear or cyclic alkyl monomer or an aryl monomer; and methods of transesterification between two polyesters, also by using one of the enzymes described herein (e.g., lipase). In particular, the method of transesterification between two polyesters includes mixing the two polyesters, adding an enzyme, such as a lipase, esterase, or protease, to the polyester mixture, and reacting the two polyesters under conditions and for a time sufficient to obtain the desired polymers.

The invention provides several advantages. First, it reduces or eliminates the use of chemical solvents and therefore significantly reduces environmental pollution caused by conventional chemical synthesis of polymers. Second, because of the chemical selectivity of enzymatic synthesis, the amount of reactants (i.e., monomers), which are required to complete a polymerization reaction and to achieve a desired amount of a polymer product, can be precisely controlled to the right stoichiometry. In other words, no excess reactants are needed, which results in lower production costs and is industrially significant. Third, because of the involvement of an enzyme, which requires that the surrounding environment be mild, the polymers that can be prepared by the enzymatic synthesis of this invention are generally biocompatible. As a result, these polymers can be used in a number of biomedical applications such as carriers for controlled drug delivery, tissue engineering, bio-implants, and scaffolds.

Unless otherwise defined, all technical and scientific terms used herein have the same meaning as commonly understood by one of ordinary skilled in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of several embodiments of the invention are set forth in the accompanying description below. Other features, objects, and advantages of the invention will be apparent from the description and drawings, and from the claims.

DETAILED DESCRIPTION

The present invention provides new polyorganosilicones and enzymatic methods of synthesizing polymers such as polyorganosilicones and polyesters. The new polyorganosilicones, and the polyorganosilicones and polyesters that can be prepared by the new methods described herein, include those of formulae (I) to (IV) below:

in which each of R, R', R", x, y, n, T, A, and B are defined above in the Summary.

These polymers can be further modified by methods known in the art. For example, the carbonyl groups can be converted to thiocarbonyl (i.e., —(C=S)—), and the T, when it is aryl, can be substituted or further substituted with substituents such as halo, hydroxy, haloalkyl, thio, carboxy, alkoxycarbonyl, acylamino, and aryl. Accordingly, the modified polymers thus obtained, as well as the modification methods, are also within the scope of this invention.

Enzymatic Synthesis of Polymers

The enzymes that can be used in the methods of this invention include those that can catalyze the reactions that result in polymer products. For instance, a lipase can be used in a polycondensation reaction that results in polymers such as polyesters (e.g., when B is oxygen in formula (II)) and polyamides (e.g., when B is amino in formula (I)). Similarly, esterases and proteases can also be used for polymerization. The enzymes can be either free in water or in liquid reactants, or immobilized, e.g., with agar gel, so that they can be recycled for repeated uses. The enzymes can be used either fresh after being isolated from culture or after being stored for an extended period of time so long as they remain active.

Suitable monomers that can be used in the new enzymatic synthesis methods include those that can undergo the new polymerization process, e.g., diacids, anhydrides, caprolatams, diols, diamines, and molecules that include polymerizable functionalities such as hydroxy, ester, thiol, thioester, and amino groups.

To carry out the new methods, one can first mix monomers described herein and an enzyme suitable for the desired type of polymerization in a suitable container or vessel, e.g., in a round bottom flask. The flask can then be placed in an oil or water bath maintained at a predetermined temperature and the monomer mixture be stirred for a period of time. By-products can be removed by nitrogen flushing, azeotropic distillation, or vacuum. The enzyme can then separated, e.g., by using water, and the product can then be purified by known methods.

The enzymatic synthesis of this invention can be conducted in mild conditions that are acceptable to enzymes. For instance, the reactions can be conducted at a temperature between 10° C. to 120° C. (e.g., 25° C. to 100 or 115° C., e.g., at 50, 60, 70, 80, 90, 100, or 110° C.). The enzymatic synthesis can also be conducted in an organic solvent-free environment, e.g., in an aqueous solution or in a solvent-free condition.

Schemes 1, 2, and 3 are self-explanatory examples of enzymatic polymerization reactions that can be used to prepare the new polyorganosilicones. The definition of each of the variables (i.e., A, B, x, y, R', R, and n) is the same as that in Formula (I). For instance, R can be, e.g., OH or $NH_2$; R' can be, e.g., hydroxy or alkoxy; R''' can be, e.g., hydrogen, hydroxy, alkyl, or alkoxy; A can be, e.g., O or NH; B can be, e.g., alkylene; and n can be, e.g., 30–120.

Schemes 4 to 6 are self-explanatory examples of enzymatic polymerization reactions that can be used to prepare the polyesters described herein. The definitions of R, R', A, B, x, and n in Schemes 4 to 6 are the same as those in formulae (II), (III), and (IV). For instance, each of A and B can be O or NH; each R can be OH or $NH_2$; each R' can be OH, H, O-alkyl, or O-aryl; and T can be aryl or alkylene.

Scheme 4

Scheme 6

Scheme 7 is a self-explanatory reaction that can be used to prepare a polyester terpolymer (i.e., a polyester having three types of monomer component). The definitions of R, R', A, B, and x are the same as those set forth above in formula (II), (III), or (IV). For instance, each of R and R' can be OH or $NH_2$; each of A and B can be O or NH; and x can be 4–50.

Scheme 7

Scheme 5

Lipases (e.g., *Candida antarctica* lipase, lipase A, and lipase B), and other enzymes such as esterases and proteases (e.g., papain and chymotrypsin), efficiently catalyze the polycondensation of various monomers as described herein, such as dimethyl 5-hydroxyisophthalate and polyethylene glycols, in a solvent-free system. As described in the examples below, the molecular weights of the polyethylene glycol units can affect the polymerization behavior. In addition, the polymer molecular weight increases under reduced pressure and at higher temperatures. The synthesized polymers can be easily functionalized, e.g., with alkyl groups of varying chain lengths carrying a polar functionality at the end of the chain. The new enzymatic reaction system affords a variety of biodegradable amphiphilic polymers via non-toxic, enzymatic catalysis under mild reaction conditions without organic solvents. Therefore, it is environmentally benign and provides an example of "Green Polymer Chemistry."

Characterization of Polymers

The polymers obtained by the new methods can be characterized by known methods. For instance, the molecular weight and molecular weight distributions can be determined by gel permeation chromatography (GPC), matrix assisted laser desorption ionization (MALDI), and static or dynamic light scattering. Whereas the physical and thermal properties of the polymer products can be evaluated by thermal gravemetric analysis (TGA), differential scanning calorimetry (DSC), or surface tensiometer; the chemical structures of the polymers can be determined by, e.g., NMR ($^1$H, $^{13}$C NMR, $^1$H-$^1$H correlation, or $^1$H-$^{13}$C correlation), IR, UV, Gas Chromatography-Electron Impact Mass Spectroscopy (GC-EIMS), EIMS, or Liquid Chromatography Mass Spectroscopy (LCMS).

Applications of the Polymers

The presence of linkages such as ester and amide linkages in the polymers described herein makes these polymers good candidates for biomedical applications. For example, they can be used as biodegradable matrices for tissue engineering. Because of the inclusion of hydrophilic groups such as ethylene oxide (i.e., when x is 2, and A and B are both oxygen) and hydrophobic groups such as carbonyl groups and siloxane groups, the polyorganosilicones and polyesters are generally amphiphilic. In aqueous solutions, the polymers can fold into specific conformations such as micelles. Thus, they can be used to trap molecules such as drugs, e.g., camptothecin, etoposide, and other anticancer, antibiotic, antiviral, and related drug molecules in aqueous media. The drugs can be released in a controlled manner when the polymers are exposed to specific conditions, e.g., when the solution temperature or pH values are changed. Alternatively, drugs can be chemically bonded to these polymers, which further sustains the release of drugs. Conjugate moieties can be attached to the polymers, e.g., to improve selectivity of drug delivery or of drug encapsulation.

The polyorganosilicones are in general chemically and thermally stable. Thus, they can be used in compositions and structures such as packaging materials, fire-retardants, and thermal insulators. In addition, polymers with free phenolic groups can be used as antioxidant agents in food materials, cooking oil, and beverages.

Upon modification with conjugated polymers, the polymers are good candidates for opto-electronic applications such as polyelectrolytes in photovoltaic devices as well as in biosensor applications.

The invention is further described in the following examples, which are only illustrative and do not in any way limit the scope of the invention described in the claims.

EXAMPLES

Example 1

Enzyme Catalyzed Synthesis of Functionalized Aromatic Polyesters

Dimethyl 5-hydroxyisophthalate (1, 1.0 mmol, 0.21 g) and polyethylene glycol (PEG) (1.0 mmol, M.W. 600 (0.6 g)(2a), 900 (0.9 g)(2b), and 1500 (1.5 g)(2c) and 300 (0.3 g)(2d)) were placed in a round-bottom flask (25 ml capacity). To this mixture was added NOVOZYME-435® (immobilized *Candida antarctica* lipase B), obtained from Novozymes, Denmark (10% by weight w.r.t. monomers, 0.80–1.7 g). The reaction flask was then placed in a constant temperature oil bath maintained at 90° C. under vacuum.

The reaction, as shown in Scheme 8 below (and in FIG. 1), was allowed to proceed for 48 hours, after which the mixture was quenched by adding chloroform and filtering off the enzyme under vacuum. The organic solvent was then evaporated under vacuum and the residue was dialyzed using a membrane with a molecular weight cutoff of 6000. After the completion of dialysis, the product polymers 3a–3d (as described in further detail below) were freeze-dried.

Scheme 8

Novozyme-435 catalyzed synthesis of functionalized aromatic polyesters

In the polymerization without enzyme (control experiment), the monomers were recovered unchanged. Furthermore, no polymer formation was observed by using the deactivated *Candida antarctica* lipase B. These data imply that the present polymerizations proceeded through lipase catalysis.

The polymerization of 1 with PEG-300 (2d) under the same reaction conditions resulted in hardly any conversion to the copolymer (3d), probably because this PEG is of low molecular weight and its amount taken (in molar ratio to 1) is much less than that in the cases of 2a–2c.

The structures of the polymers were characterized using NMR spectroscopy (Bruker 500 MHz); and the molecular weights of the polymer products were determined by Gel Permeation Chromatography (GPC). The number average molecular weight of the polymers 3a–3c was found to be between 18000–23000 Da. The NMR results are indicated below.

Poly [(poly (oxyethylene-600)-oxy-5-hydroxyisophthaloyl] (3a)

This polymer was obtained by heating dimethyl 5-hydroxyisophthalate (1 mmol, 0.21 g) with PEG 600 (1 mmol, 0.6 g) in presence of Novozyme-435 (0.8 g) at 90° C. in solvent free condition for 48 hours under vacuum. It was obtained as a viscous oil after freeze-drying in 90% yield.

$^1$H NMR Data (CDCl$_3$): δ 3.64–3.68 (brs, methylene PEG protons on C-9 and C-10 carbons of the repeating units and on C-α and C-β), 3.82 (t, 2H, C-8H), 3.93 (s, 3H, —COOCH$_3$), 4.48 (t, 2H, C-7H), 7.71 (m, 2H, C-4H and C-6H) and 8.21 (s, 1H, C-2H).

$^{13}$C NMR Data (CDCl$_3$): δ 52.74 (—OCH$_3$ end group), 62.07 (C-α), 64.74 (C-β), 69.44 (C-8), 70.93 (repeating PEG units' carbons), 72.90 (C-7), 121.43 (C-4 and C-6), 122.53 (C-2), 131.18 (C-1 and C-3), 157.57 (C-5) and 166.11 (—COOMe).

Poly [(poly (oxyethylene-900)-oxy-5-hydroxyisophthaloyl](3b)

This polymer was obtained by condensing dimethyl 5-hydroxyisophthalate (1 mmol, 0.21 g) with PEG 900 (1 mmol, 0.9 g) in presence of Novozyme-435 (1.1 g) at 90° C. in solvent free condition for 48 hours under vacuum. It was obtained as a waxy solid after freeze-drying in 93% yield.

$^1$H NMR Data (CDCl$_3$): δ 3.63–3.81 (brs, methylene PEG protons on C-9 and C-10 carbons of the repeating units and on C-α and C-β), 3.82 (t, 2H, C-8H), 3.92 (s, 3H, —COOCH$_3$), 4.46 (t, 2H, C-7H), 7.69 (d, 2H, C-4H and C-6H) and 8.73 (s, 1H, C-2H).

$^{13}$C NMR Data (CDCl$_3$): δ 52.73 (—OCH$_3$ end group), 62.07 (C-α), 64.72(C-β), 69.43 (C-8), 70.90 (repeating PEG units' carbons), 72.89 (C-7), 121.43 (C-4 and C-6), 122.51 (C-2), 131.99 (C-1 and C-3), 157.56 (C-5) and 166.38 (—COOMe).

Poly [(poly (oxyethylene-1500)-oxy-5-hydroxyisophthaloyl] (3c)

This polymer was obtained by heating dimethyl 5-hydroxyisophthalate (1 mmol, 0.21 g) with PEG 1500 (1 mmol, 1.5 g) in the presence of Novozyme-435 (1.7 g) at 90° C. in solvent free condition for 48 hours under vacuum. It was obtained as a white solid after freeze-drying in 90% yield.

$^1$H NMR Data (CDCl$_3$): δ 3.6–3.79 (brs, methylene PEG protons on C-9 and C-10 carbons of the repeating units and on C-α and C-β), 3.86(t, 2H, C-8H), 3.96 (s, 3H, —COOCH$_3$ end group), 4.51 (t, 2H, C-7H), 7.75 (s, 2H, C-4H and C-6H) and 8.24 (s, 1H, C-2H).

$^{13}$C NMR Data (CDCl$_3$): δ 52.69 (—OCH$_3$ end group), 62.02 (C-α), 64.70(C-β), 69.43 (C-8), 70.90 (repeating PEG units' carbons), 72.91 (C-7), 121.48 (C-4 and C-6), 122.38 (C-2), 131.95 (C-1 and C-3), 157.62 (C-5) and 166.07 (—COOMe).

Example 2

Functionalization of Poly [(poly (oxyethylene)-oxy-5-hydroxyisophthaloyl] (3a, 3b and 3c)

Figure 1:
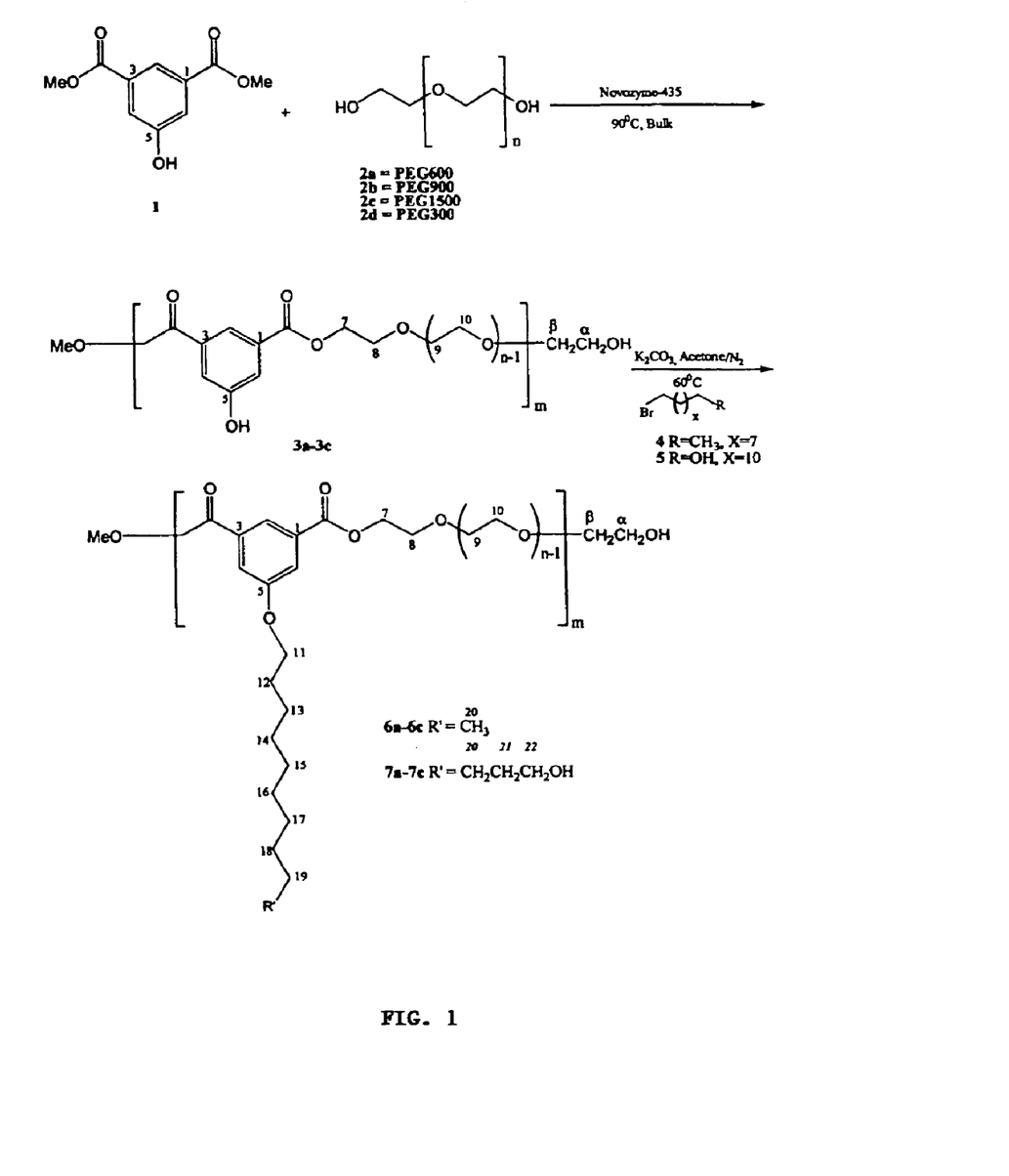
FIG. 1 is a reaction scheme used in the Examples.

The polymers 3a–3c were functionalized by coupling them with bromodecane (4) and 12-bromododecanol (5) using anhydrous potassium carbonate and acetone as shown in FIG. 1. A general method to carry out this coupling reaction is as follows.

Equimolar quantities of 3a–3c (0.8, 1.1 and 1.7 g), from Example 1, and bromodecane 4 or 12-bromododecanol 5 (0.22 or 0.26 g) were dissolved in dry acetone (10 ml). To the resultant solution was added an equimolar amount of anhydrous potassium carbonate (0.13 g). The reaction mixture was refluxed at 60° C. and the progress of the reaction was monitored by TLC using ethyl acetate in petroleum ether (30%). After completion, potassium carbonate was removed by filtration and the solvent was removed under vacuum to give the products 6a–6c and 7a–7c from 4 and 5, respectively (as shown in FIG. 1 and as described in further detail below).

The structures of the functionalized polymers were established by $^1$H, $^{13}$C NMR spectra and also by their $^1$H-$^1$H correlation spectrum (COSY). The results are described below.

Poly[(polyoxyethylene-600)-oxy-5-decanyloxyisophthaloyl] (6a)

$^1$H NMR Data (CDCl$_3$): δ 0.86–0.92 (bs, 3H C-20H), 1.27–1.38 (m, C-13H to C-19H), 1.75–1.85 (m, 2H, C-12H), 3.65–3.67 (brs, methylene PEG protons on C-9 and C-10 carbons of the repeating units and on C-α and C-β), 3.76 (t, 2H, C-8H), 3.95 (s, 3H, —COOCH$_3$ end group), 4.06 (t, 2H, C-11H), 4.51 (t, 2H, C-7H), 7.75 (m, 2H, C-4H and C-6H) and 8.36 (s, 1H,C-2H).

$^{13}$C NMR Data (CDCl$_3$): δ 14.52 (C-20), 23.05–32.26 (C-12 to C-19), 52.79 (—OCH$_3$ end group), 61.76 (C-α), 64.81 (C-β), 69.46 (C-8 and C-11), 70.38–70.95 (repeating PEG units' carbons), 72.87 (C-7), 120.04 (C-4 and C-6), 123.32 (C-2), 131.99 (C-1 and C-3), 159.53 (C-5) and 166.07 (—COOMe).

Poly[(polyoxyethylene-900)-oxy-5-decanyloxyisophthaloyl] (6b)

$^1$H NMR Data (CDCl$_3$): δ 0.75–0.87 (bs, 3H, C-20H), 1.25–1.36 (m, C-13H to C-19H), 1.77–1.83 (m, 2H, C-12H), 3.66–3.69 (brs, methylene PEG protons on C-9 and C-10 carbons of the repeating units and on C-α and C-β), 3.82 (bs, 2H, C-8H), 3.96 (s, 3H, —COOMe end group), 4.03–4.06 (t, 2H, C-1H), 4.51 (t, 2H, C-7H), 7.77 (m, 2H, C-4H and C-6H) and 8.30 (s, 2, C-2H).

$^{13}$C NMR Data (CDCl$_3$): δ 14.50 (C-20), 23.03–32.24 (C-12 to C-19), 52.77 (—OCH$_3$ end group), 61.86 (C-α), 64.80 (C-β), 69.45 (C-8 and C-11), 70.46–70.87 (repeating PEG units' carbons), 72.86 (C-7), 120.26 (C-4 and C-6), 123.16 (C-2), 131.98 (C-1 and C-3), 159.53 (C-5) and 166.06 (—COOMe).

Poly[(polyoxyethylene-1500)-oxy-5-decanyloxyisophthaloyl] (6c)

$^1$H NMR Data (CDCl$_3$): δ 0.90 (t, 3H C-20H), 1.31 (m, C-13H to C-19H), 1.81 (m, 2H, C-12H), 3.66–3.69 (brs, methylene PEG protons on C-9 and C-10 carbons of the repeating units and on C-α and C-β carbons), 3.87 (t, 2H, C-8H), 3.96 (s, 3H, —COOCH$_3$ end group), 4.10 (t, 2H, C-11H), 4.51 (t, 2H, C-7H), 7.77 (m, 2H, C-4H and C-6H) and 8.30 (s, 1H, C-2H).

$^{13}$C NMR Data (CDCl$_3$): δ 14.54 (C-20), 23.06–32.26 (C-12 to C-19), 52.80 (—OCH$_3$ end group), 61.89 (C-α), 64.76 (C-β), 69.22 (C-8 and C-11), 70.52–70.91 (repeating PEG units' carbons), 72.87 (C-7), 120.26 (C-4 and C-6), 123.34 (C-2), 131.99 (C—I and C-3), 159.53 (C-5) and 166.08 (—COOMe).

Poly[(polyoxyethylene-600)-oxy-5-(12-hydroxydodecanyloxy)-isophthaloyl] (7a)

$^1$H NMR Data (CDCl$_3$): δ 1.31 (bs, C-13H to C-20H), 1.54–1.57 (m, 2H, C-21H), 1.82 (m, 2H, C-12H), 3.31–3.43 (t, 2H, C-22H), 3.60–3.67 (brs, methylene PEG protons on C-9 and C-10 carbons of the repeating units and on C-α and Cβ carbons), 3.86 (t, 2H, C-8H), 3.95 (s, 3H, —COOCH$_3$ end group), 4.05 (t, 2H, C-11H), 4.51 (t, 2H, C-7H), 7.76 (bs, 2H, C-4H and C-6H) and 8.28 (s, 1H, C-2H).

$^{13}$C NMR Data (CDCl$_3$): δ 26.16–33.15 (C-12 to C-21), 52.80 (—OCH$_3$ end group), 61.82 (C-α), 63.23 (C-22), 64.83 (C-β), 69.49 (C-8 and C-11), 70.45–70.96 (repeating PEG units' carbons), 72.94 (C-7), 120.26 (C-4 and C-6), 123.34 (C-2), 132.02 (C-1 and C-3), 159.57 (C-5) and 166.07 (—COOMe).

Poly[(polyoxyethylene-900)-oxy-5-(12-hydroxydodecanyloxy)-isophthaloyl] (7b)

$^1$H NMR Data (CDCl$_3$): δ 1.29 (bs, C-13H to C-20H), 1.43–1.49 (m, 2H, C-21H), 1.78–1.85 (m, 2H, C-12H), 3.37–3.47 (t, 2H, C-22H), 3.60–3.68 (brs, methylene PEG protons on C-9 and C-10 carbons of the repeating units and on C-α and C-β carbons), 3.86 (t, 2H, C-8H), 3.94 (s, 3H, —COOCH$_3$ end group), 4.05 (t, 2H, C-11H), 4.51 (t, 2H, C-7H), 7.76 (m, 2H, C-4H and C-6H) and 8.21 (s, 1H, C-2H).

$^{13}$C NMR Data (CDCl$_3$): δ 26.16–33.20 (C-12 to C-21), 52.83 (—OCH$_3$ end group), 61.82 (C-α), 63.38 (C-22), 64.84 (C-β), 69.00 (C-8 and C-11), 70.93 (repeating PEG units' carbons), 72.90 (C-7), 120.34 (C-4 and C-6), 123.38 (C-2), 132.02 (C-1 and C-3), 159.54 (C-5) and 166.12 (—COOMe).

Poly[(polyoxyethylene-1500)-oxy-5-(12-hydroxydodecanyloxy)-isophthaloyl] (7c)

$^1$H NMR Data (CDCl$_3$): δ 1.31 (bs, C-13H to C-20H), 1.54–1.57 (m, 2H, C-21H), 1.82 (bs, 2H, C-12H), 3.43 (t, 2H, C-22H), 3.67–3.74 (brs, methylene PEG protons on C-9 and C-10 carbons of the repeating units and on C-α and C-β carbons), 3.86 (t, 2H, C-8H), 3.95 (s, 3H, —COOCH$_3$ end group), 4.05 (t, 2H, C-11H), 4.51 (t, 2H, C-7H), 7.76 (bs, 2H, C-4H and 8.28 (s, 1H, C-2H).

$^{13}$C NMR Data (CDCl$_3$): δ 26.15–33.18 (C-12 to C-21), 52.82 (—OCH$_3$ end group), 61.82 (C-α), 63.36 (C-22), 64.83 (C-β), 69.49 (C-8 and C-11), 70.90 (repeating PEG units' carbons), 72.89 (C-7), 120.33 (C-4 and C-6), 123.37 (C-2), 132.01 (C-1 and C-3), 159.52 (C-5) and 166.07 (—COOMe).

Example 3

Effect of Time on the Rate of Polymerization

Effects of reaction time were investigated in the copolymerization of dimethyl 5-hydroxyisophthalate and PEG-1500 using Novozyme-435 as a catalyst.

Copolymerization was carried out for different time periods to find the optimum conditions with PEG-1500 (2c) and dimethyl 5-hydroxyisophthalate (1). In a typical experiment, equimolar proportions of 1 and 2c were added along with the enzyme (10% w.r.t. the monomers) and the reaction was allowed to proceed at different time intervals, i.e., 2, 4, 12, 20, and 48 hours at 90° C. and under bulk conditions.

Figure 2:
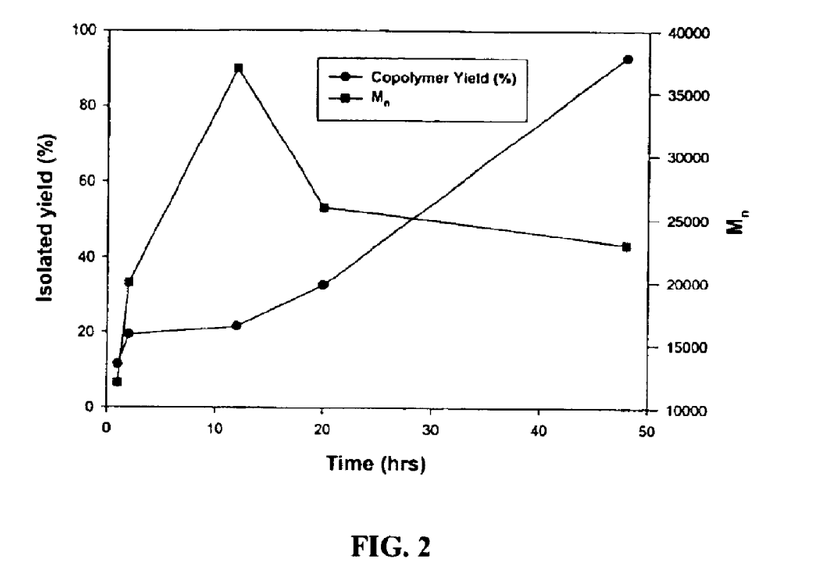
FIG. 2 is a graph showing the effect of reaction time on polymer yield.

FIG. 2 shows a plot of the copolymer yield and number average molecular weight (Mn) versus reaction time in the copolymerization of dimethyl-5-hydroxyisophthalate (1) and PEG-1500 (2c) using lipase (Novozyme-435) as the catalyst in bulk. In the first 12 hours, the copolymer yield and Mn increased rapidly to 22% and 37000, respectively. Further increase in copolymer yield with increased reaction time occurred gradually. By 48 hours, the copolymer yield and Mn were 93% and 23000, respectively. The Mn increased for reaction times up to 12 hours and then decreased by 37% from 12 hours to 48 hours. However, after 48 hours, the conversion of monomers was almost quantitative. The molecular weight distribution (Mw/Mn) increased up to 12 hours and then decreased with reaction time (i.e., 2.7 and 1.8 after 12 hours and 48 hours, respectively).

Such decreases in molecular weight and molecular weight distributions at extended reaction times are contrary to what is known in thermal polymerization reactions. This indicates that the enzyme started cleaving the big chains and showed selectivity towards the length of the polymer. The results of the kinetic study are also shown in FIG. 2.

Example 4

Effect of Temperature on the Rate of Polymerization

Effects of reaction temperature were investigated in the copolymerization of dimethyl 5-hydroxyisophthalate and PEG-1500 using Novozyme-435 as a catalyst.

Copolymerization was carried out at different temperatures to find the optimum conditions with PEG-1500 (2c) and dimethyl 5-hydroxyisophthalate (1). To determine the effect of temperature on the rate of polymerization, the same polymerization reaction as in Example 3 was carried out at different temperatures, i.e., 40, 60, 70, 80, and 90° C., and allowed to proceed for 48 hours in each case. After the usual work-up, the polymer products were isolated and molecular weights determined. The number average molecular weights of the polymers obtained in the temperature range 40° to 80° C. ranged between 12,000 and 15,000 Da, but at 90° C., the molecular weight changed dramatically to 23,000 Da. Interestingly, the copolymer isolated yield also increased with the increase in temperature and was nearly quantitative at 90° C.

Table 1 below shows the results.

TABLE 1

| S. No. | Temperature | Isolated Yield (%) | Molecular Weight (M$_n$) |
|---|---|---|---|
| 1. | 40° C. | 37.4 | 12000 |
| 2. | 60° C. | 43.7 | 13000 |
| 3. | 70° C. | 46.7 | 12000 |
| 4. | 80° C. | 65.5 | 15000 |
| 5. | 90° C. | 93.5 | 23000 |

Example 5

Lipase Catalyzed Synthesis of a Polyorganosilicone

Dimethyl 5-hydroxyisophthalate (0.210 g, molecular weight 1000, 1.0 mmol) and carbinol (i.e., hydroxyl) terminated polydimethylsiloxane (0.100 g, molecular weight 900–1000, 1.0 mmol) monomers, both from Gelest, Inc., were mixed in a round-bottom flask under nitrogen. To this mixture was added 10% by weight (with respect to the weight of the monomers) NOVOZYME-435®. The resulting mixture was used in a reaction shown below in Scheme 9 at 90° C. for a predetermined time, vacuum was applied, and aliquots of the mixture were taken at different time periods until the reaction was completed. After completion, an organic solvent was added and the enzyme was filtered off to quench the reaction. The organic solvent was then removed under reduced pressure to obtain a polyorganosilicone.

Scheme 9

Novozyme-435® catalyzed synthesis of polyorganosilicone.

The structure of the polymer formed was analyzed from its detailed spectral studies, i.e.

$^1$H NMR, $^{13}$C NMR and $^1$H-$^1$H correlation spectra. Comparison of the $^1$H NMR spectrum of the monomer and the polymer showed the appearance of a new signal at δ4.30 and disappearance of the signal at δ3.6 in the polymer spectra (spectra not shown). This indicates a transesterification between the CH$_2$OH of the silicon diol and the dimethyl ester. The signal at δ4.30 in the polymer was assigned to the methylene protons of the CH$_2$OCO moiety. The transesterification reaction between the silicon diol and the dimethyl ester was also confirmed from the $^{13}$C NMR spectrum of the product polymer, which showed a signal at δ165.0 for the carbonyl carbon of the newly formed ester moiety.

Example 6

Effect of Time on Reaction Kinetics

Figure 3:
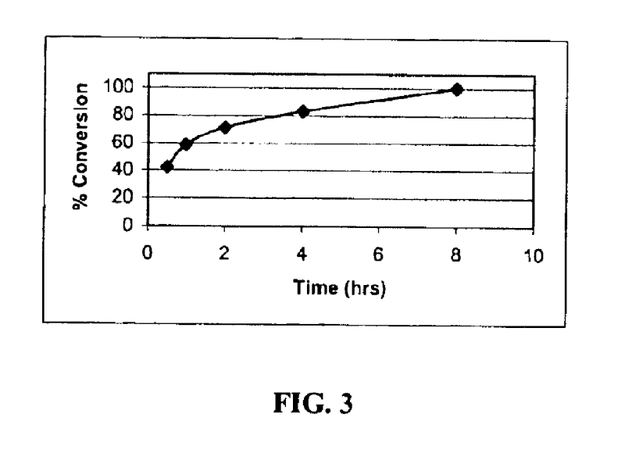
FIG. 3 is a graph showing the effect of reaction time on the conversion rate of monomers in synthesizing polyorganosilicones.

The polymerization of Example 5 was carried out for different time periods to study the reaction kinetics. The percent conversion of monomers to copolymers was determined by 1H NMR spectroscopy. FIG. 3 shows the effect of reaction time period on the conversion of the monomer to the polyorganosilicone. It was observed that with the increase in reaction time, the conversion of monomers to the polyorganosilicone increased. After 8 hours, all the monomers were converted to polymers.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polyorganosilicone of the formula:

wherein
each R', independently is a hydroxy or alkoxy; each R", independently is a hydrogen, alkyl, alkoxy, aryl, or aryloxy;
each x, independently, is an integral of 1 to 10;
y is an integral of 1 to 1,000;
n is an integral of 1 to 10,000;
A is O or NH; and
B is alkylene, arylene, or oxaalkylene.

2. A polyorganosilicone of claim 1, wherein x is ten; y is 1000; and n is 10000.

3. A method of synthesizing a polyorganosilicone polymer of claim 1, the method comprising:
mixing linear or cyclic monomers, oligomers, macromers, or a combination thereof to form a monomer mixture;
adding a lipase, esterase, or protease to the monomer mixture to form a reaction mixture; and
reacting the reaction mixture for a time and under polymerizing conditions suitable to obtain the polyorganosilicone polymer.

4. The method of claim 3, further comprising mixing the polymer with a fire-retardant.

5. A method of retarding fire, the method comprising using the polyorganosilicone polymer of claim 1 as a fire-retardant.

6. A method of controlled drug delivery, the method comprising using the polyorganosilicone polymer of claim 1 as a carrier for controlled drug delivery.

7. A method of delivering bio-implants, the method comprising using the polyorganosilicone polymer of claim 1 as a carrier for bio-implants.

8. A method of tissue engineering, the method comprising using the polyorganosilicone polymer of claim 1 as a biodegradable matrix for tissue engineering.

9. A packaging material comprising the polyorganosilicone polymer of claim 1.

10. A thermal insulator comprising the polyorganosilicone polymer of claim 1.

11. An antioxidant agent comprising the polyorganosilicone polymer of claim 1, and free phenolic groups.

12. A photovoltaic device comprising a polyorganosilicone polymer of claim 1, and conjugated polymers.

13. A biosensor device comprising a polyorganosilicone polymer of claim 1, and conjugated polymers.

14. A composition or structure comprising a polyorganosilicone of the formula:

wherein each R', independently is a hydroxy or alkoxy; each R", independently is a hydrogen, alkyl, alkoxy, aryl, or aryloxy;

each x, independently, is an integral of 1 to 10;

y is an integral of 1 to 1,000;

n is an integral of 1 to 10,000;

A is O or NH; and

B is alkylene, arylene, or oxaalkylene.

15. The composition of claim 14, further comprising a fire retardant.

16. A method of retarding fire, the method comprising using the composition or structure of claim 15 as a fire-retardant.

* * * * *

UNITED STATES PATENT AND TRADEMARK OFFICE
CERTIFICATE OF CORRECTION

| | | |
|---|---|---|
| PATENT NO. | : 6,962,963 B2 | Page 1 of 1 |
| APPLICATION NO. | : 10/688582 | |
| DATED | : November 8, 2005 | |
| INVENTOR(S) | : Kumar et al. | |

It is certified that error appears in the above-identified patent and that said Letters Patent is hereby corrected as shown below:

Title Page item 73
Please add the following data:

Col. 1 line 9
Please insert before TECHNICAL FIELD section --The invention described herein may be manufactured, used and licensed by or for the U.S. Government for U.S. Governmental purposes without the payment to us of any royalty thereon. This invention was developed under Contract No DAAD 16-01-C-0011 with the U.S. Army Natick Soldier Systems Center, Natick, MA 01760.--

Signed and Sealed this

Twenty-fourth Day of March, 2009

JOHN DOLL
*Acting Director of the United States Patent and Trademark Office*